US008105632B2

(12) United States Patent
Jy et al.

(10) Patent No.: US 8,105,632 B2
(45) Date of Patent: Jan. 31, 2012

(54) CELL-DERIVED MICROPARTICLES AS HEMOSTATIC AGENTS FOR CONTROL OF HEMORRHAGE AND TREATMENT OF BLEEDING DISORDERS

(75) Inventors: Wenche Jy, Miami, FL (US); Joaquin J. Jimenez, Miami, FL (US); Lawrence L. Horstmann, Miami, FL (US); Yeon S. Ahn, Miami, FL (US); Eugene Ahn, Miami, FL (US)

(73) Assignee: University of Miami, Miami, FL (US)

( * ) Notice: Subject to any disclaimer, the term of this patent is extended or adjusted under 35 U.S.C. 154(b) by 985 days.

(21) Appl. No.: 11/792,399

(22) PCT Filed: Dec. 7, 2005

(86) PCT No.: PCT/US2005/044064
§ 371 (c)(1),
(2), (4) Date: Oct. 15, 2007

(87) PCT Pub. No.: WO2006/062945
PCT Pub. Date: Jun. 15, 2006

(65) Prior Publication Data
US 2008/0069807 A1 Mar. 20, 2008

Related U.S. Application Data

(60) Provisional application No. 60/633,417, filed on Dec. 7, 2004.

(51) Int. Cl.
*A61K 35/18* (2006.01)
(52) U.S. Cl. .................. 424/533; 424/93.73; 424/529
(58) Field of Classification Search ............... 424/93.73, 424/533, 529
See application file for complete search history.

(56) References Cited

FOREIGN PATENT DOCUMENTS
WO WO 00/29029 A1 5/2000

OTHER PUBLICATIONS

Piacibello et al, 2000. Ex vivo expansion of megakaryocytes. Transfusion Science, vol. 22:107-110).*
Solheim and Wesenberg, 2001. Rational use of blood products. European Journal of Cancer, vol. 37:2421-2427.*
Levi M. et al., "Fibrinogen-Coted Albumin Microcapsules Reduce Bleeding in Severely Thrombocytopenic Rabbits", Nature Medicine, Jan. 1999, vol. 5, No. 1, p. 107-111.
McGill M. et al., "Platelet Membrane Vesicles Reduced Microvascular Bleeding Times in Thrombocytopenic Rabbits", The Journal of Laboratory and Clinical Medicine, Feb. 1987, vol. 109, No. 2, p. 127-133.
Combes V. et al., "In Vitro Generation of Endothelial Microparticles and Possible Prothrombotic Activity in Patients With Lupus Anticoagulant" The Journal of Clinical Investigation, Jul. 1999, vol. 104, No. 1, p. 93-102.
Biro E. et al., "Human Cell-Derived Microparticles Promote Thrombus Formation In Vivo in a Tissue Factor-Dependent Manner.", Journal of Thrombosis and Haemostasis:, Dec. 2003, vol. 1, No. 12, p. 2561-2568.
Levi M. et al., "Fibrinogen-Coted Albumin Microcapsules Reduce Bleeding in Severely Thrombocytopenic Rabbits", Nature Medicine, Jan. 1999, vol. 5, No. 1, p. 107-111.
Ahn, "Cell-Derived Microparticles: 'Miniature Envoys With Many Faces'", *Journal of Thrombosis and Haemostasis*, 3: 884-887, 2005.
George, et al., "Isolation of Human Platelet Membrane Microparticles From Plasma and Serum", *Blood*, 60. 4, 1982.
Jimenez et al., "Endothelial Cells Release Phenotypically and Quantitatively Distinct Microparticles in Activation and Apoptosis", *Thrombosis Research*, 109, 175-180, 2003.
Wenche et al., "Clinical Significance of Platelet Microparticles in Autoimmune Thrombocytopenias", *The Journal of Laboratory and Clinical Medicine*, 119, No. 4, 334-345, 1992.
Wolf, "The Nature and Significance of Platelet Products in Human Plasma", *Brit. J. Haernat*, 13, 269-288, 1967.
Warkenton, T.E., An Overview of the Heparin-Induced Thrombocytopenia Syndrome. Seminars in Thrombosis and Homeostasis, vol. 30, No. 3, 2004.
Mallat et al., Elevated levels of Shed Membrane Microparticle with Procoagulant potential in the peripheral circulating blood of patients with acute coronary syndromes, Circulation, vol. 101, p. 841-843, 2000.

* cited by examiner

*Primary Examiner* — Blaine Lankford, Jr.
(74) *Attorney, Agent, or Firm* — Venable LLP; Stefan J. Kirchanski (57) ABSTRACT

Compositions comprising membrane-derived and synthetic microparticles that induce platelet aggregation and are useful for treating bleeding disorders, particularly those involving platelet dysfunction. Microparticles include endothelial derived microparticles (EMP), platelet derived microparticles (PMP), erythrocyte derived microparticles (RMP), and synthetic microparticles (SMP), and are used to treat disorders such as thrombocytopenia caused by chemotherapy.

13 Claims, 8 Drawing Sheets

CELL-DERIVED MICROPARTICLES AS HEMOSTATIC AGENTS FOR CONTROL OF HEMORRHAGE AND TREATMENT OF BLEEDING DISORDERS

This application is a 371 of PCT/US2005/044064, filed Dec. 7, 2005 and claims priority to U.S. provisional application No. 60/633,417, filed Dec. 7, 2004, each of which is hereby incorporated by reference.

BACKGROUND OF THE INVENTION

1. Field of the Invention

The invention relates to compositions comprising membrane-derived microparticles that promote platelet adhesion, aggregation, blood clot formation and to a method for treating bleeding disorders, particularly blood coagulation disorders, platelet function disorders in the instance of low platelet counts. The invention is also useful in minimizing blood loss in a mammal, in particular in patients with trauma, patients undergoing surgical or medical invasive procedures where blood loss can be substantial.

2. Background (A) Clinical Bleeding Disorders (B) Cell-Derived Microparticles (C-MP).

2(A). Clinical Bleeding Disorders

A number of medical disorders manifesting prolonged bleeding can be classified into (i) platelet disorders, (ii) clotting disorders and (iii) ill defined bleeding disorders.

(i) Platelet Disorders. Patients with platelet disorders often bleed excessively because number of platelets are insufficient (thrombocytopenia) or platelet function is impaired, although platelet counts are normal (platelet dysfunction). For example, patients with idiopathic thrombocytopenic purpura (ITP) have insufficient platelets and suffer from easy bruising and bleeding. Thrombocytopenia (low platelet counts) may be caused by medications, especially following intensive chemotherapy regimens. Many drugs, e.g. aspirin, impair platelet function, leading to excessive bleeding although patients platelet counts may be normal. Some systemic illness also may cause acquired form of platelet disorders. Thrombocytopenias or platelet dysfunctions may be congenital or acquired.

(ii) Clotting Disorders. A group of genetic bleeding disorders, including von Willebrand disease (vWd) and other coagulation disorders, are characterized by the commonality of prolonged bleeding. In many of these patients with clotting disorders there is an insufficiency in the amount and/or function of clotting factors such as factor eight (FVIII) or von Willebrand factor (vWf) in blood or other clotting factors. vWf promotes platelet adhesion, aggregation and carries clotting factor VIII (FVIII). FVIII is essential for generation of thrombin and subsequent blood coagulation.

(iii) There are many ill defined bleeding disorders, some of which involve blood vessel wall.

Although various treatments are available for bleeding disorders, there is a need for treatment methods with increased efficacy and/or reduced side effects.

For example, currently, transfusion of allogeneic blood products (blood products from donors, not the patient) such as platelets and coagulation factors is the mainstay of treatment of bleeding disorders. However, such agents pose a risk of transmitting blood borne infections such as hepatitis, HIV virus and can induce immune mediated transfusion reactions. To circumvent these problems, production of recombinant clotting factors or effective small molecules is actively pursued. Some such agents are available for clinical use (Coagulin-A®, Kogenate®, for example), however, these are still very expensive and all patients are not responsive to these agents. Other treatments comprise administering human purified vWf or a cryoprecipitate of human plasma containing vWf. Directly injected vWf has a very short clearance time, further complicating therapy. Moreover, some patients reject foreign proteins and do not respond to these replacement therapies. Other hemostatic agents such as desmopressin (DDAVP) are used to treat some patients of hemophilia and vWd, but many patients do not respond to this treatment. Thus there remains a need for new treatments for bleeding disorders wherein spontaneous or trauma induced bleeding are frequent complications, sometimes life threatening.

The present invention addresses all of these problems by development of an effective, safe treatment using autologous blood products or heterologous blood products with reduced capacity for transmission of blood borne pathogen and reduced capacity of immune response induction. This method will improve the quality of life in patients with bleeding disorders and save many lives and additionally resolve a serious shortage of blood supply, an increasing problem in transfusion medicine.

2(B). Cell-derived Microparticles (MP)

Release of cell membrane-derived microparticles (MP) has been demonstrated during cell activation or apoptosis. Release of MP has been demonstrated from platelets (PMP), leukocytes (LMP), red cells (RMP) and endothelial cells (EMP) (1-3). Most MP expose procoagulant anionic phospholipids such as phosphatidylserine (PS) (4-7), having platelet factor 3 activity (PF3) (8). This activity is believed to be a major function of MP in vivo. More recently, tissue factor (TF) has been identified on leukocyte MP (LMP) (9-11), endothelial MP (EMP) (11-14), and platelet MP (PMP) (10, 15) further suggesting important roles in hemostasis and thrombosis. Prior this disclosure, TF has not been localized on RMP.

The current inventors have previously demonstrated that PMP, LMP, EMP play important roles in hemostasis and thrombosis and inflammation (1-3). They reported that surface antigens on EMP are distinctive but vary depending on the type of endothelial cell injury, e.g. apoptosis, activation (34). EMP have been shown to exhibit procoagulant activity and to be related to many thrombotic and inflammatory conditions, including lupus, MS and other chronic inflammatory disorders (2, 3, 10). EMP is further known to carry tissue factor (TF). Nevertheless, a functional role of MP in disease amelioration has not been disclosed. It was the hypothesis of the current inventors that because MPs are procoagulant, they could be exploited as therapeutic agents in bleeding disorders (3).

Coller and colleagues conjugated RGD to red cells to make them hemostatically active and named the product thromboerythrocytes in 1992 [(53) and U.S. Pat. No. 5,328,840)]. However, the Coller invention does not disclose nor anticipate the uses of the microparticles of the present invention. Other hemostatic liposome preparations have been reported, including conjugation of clotting factors such as FVIII (54, 55) and fibrinogen (56,57) to them or albumin particles to produce hemostatically active vesicles.

Chemical modifications of artificial liposomes include platelet specific adhesion molecules such as GpIIb/IIIa and Ib/IX conjugated to synthetic liposomes or to albumin to produce "artificial platelets" (58-61).

There are disadvantages to these approaches. Synthetic microparticles may activate complement cascade, creating adverse complications and may induce immune reactions, leading to autoimmune responses. No method using synthetic MP or blood cells has yet emerged as clinically practicable and there are little follow-up clinical studies.

The present invention employs novel microparticles (MP), in particular red cell microparticles (RMP), as agents for this purpose. In one embodiment, cell derived microparticles are conjugates to a protein or factor absent in a patient. In the preferred embodiment, autologous cell-derived red cell microparticles are used as hemostatic agents. This embodiment of the method has clear advantages: because the composition is autologous, one avoids immune system activation often cause by allogeneic transfusions or synthetic substances and eliminates risk of transmission of blood-borne pathogenic agents. Because red cells are the most abundant blood cell, a small fraction of blood (50-100 ml of blood from whole blood volume over 5000 ml) can be drawn safely from patients and RMP can be generated to be infused back to the same patients. The supply of the composition is safe and convenient for the patient.

SUMMARY OF THE INVENTION

The present invention relates to compositions and methods for using cell-derived microparticles (MP) or their chemically modified variants to reduce bleeding.

Endothelial microparticles (EMP), platelet derived microparticles (PMP), red cell derived microparticles (RMP), and synthetic microparticles (SMP) of similar composition/function or their chemically modified variants can be used to promote blood clotting and to enhance platelet adhesion and aggregation, improve clotting efficiency and shorten bleeding time in a variety of diseases and disorders, including, but not limited to, immune or idiopathic thrombocytopenic purpura (ITP), drug- and chemotherapy-induced thrombocytopenia and other thrombocytopenias of various causes, coagulation disorders including von Willebrand disease, hemophilia, and other bleeding disorders. It is also envisioned that the invention includes a chemical modification of MP that will enhance the desired biological property of the MP. Recombinant and purified replacement factors are available commercially and are well known in the art. Without being limited to a mechanism, the inventors believe that the microparticles function by causing more efficient platelet adhesion and aggregation at the initiation of coagulation, at least in part by providing clotting factors such as a form of vWf, FVIII or similar substance(s) on the surface of the microparticles, thereby promoting and accelerating blood clot formation. Nonetheless, the inventors do not intend to be bound by this or any other theory.

Microparticles suitable for use in the invention may be formulated in a variety of ways. EMP can be made, for example, by culturing EC (e.g. of renal, brain, or coronary origin), activating the cells with tumor necrosis factor alpha (TNF-α) to induce EMP generation, and sedimenting and washing the resulting EMP from the culture supernatant.

PMP can be generated by incubating platelets with stimulating agonists such as ADP, collagens, epinephrine or thrombin.

RMP can be generated by sonication or incubation with calcium ionophores.

MP thus generated may be modified to further increase their efficiency to promote blood clotting for specific purposes.

Figure 13:
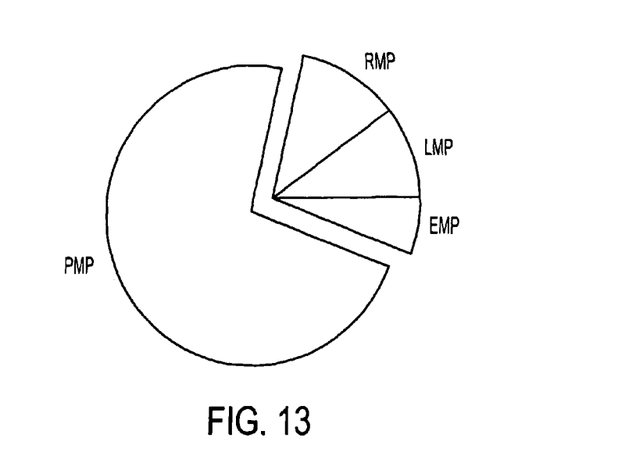
FIG. 13. Relative abundance of cell-derived microparticles in normal blood. The numbers of PMP, EMP, LMP, and RMP in plasma were assayed by flow cytometry. The pie chart shows the relative abundance of these four types of microparticles in normal plasma.
Figure 14:
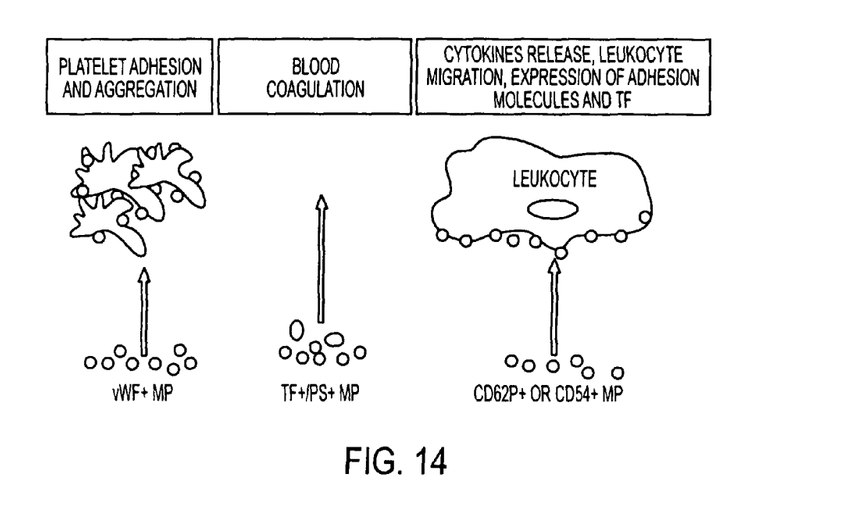
FIG. 14. Different species of microparticles exert different hemostatic functions. As shown in the figure, vWf+microparticles induce platelet adhesion and aggregation. TF+/PS+ microparticles initiate and promote blood coagulation. CD62+/CD54+ microparticles serve as diffusible messengers to activate leukocytes.

In normal blood, we found that the relative abundance of PMP, EMP, LMP, and RMP is 50-70%, 5-10%, 10-15%, and 10-15% of total MP, respectively (FIG. 13) (63). Different species of microparticles show different hemostatic functions (FIG. 14) (63).

The microparticles may be administered by any convenient and effective means known to those of skill in the art, particularly intravenously, or by direct application (e.g. topically, or by injection) to a site where hemostasis is needed or desired. Such means will be known and/or easily determined without undue experimentation.

Accordingly, it is one object to provide a method of increasing hemostasis comprising administering a composition comprising microparticles that promote blood coagulation or stimulate platelet adhesion, aggregation, clot formation to a mammal in need thereof. This is intended to include any mammal in which it is desired to increase hemostasis, particularly a human.

It is a further object of the invention to provide pharmaceutical compositions comprising microparticles as described herein that can be used according to the method of the invention. The pharmaceutical compositions typically include at least pharmaceutically acceptable diluent, excipient and/or carrier.

By "pharmaceutically acceptable diluents, excipients and carriers" is meant such compounds as will be known to persons of skill in the art as being compatible with the microparticles and suitable for local or systemic administration to an animal, particularly a human or other mammal, according to the invention. For example, the microparticles may be delivered in an acceptable aqueous vehicle, e.g. a physiologically acceptable saline. Useful solutions can be prepared by any of the methods well known in the pharmaceutical arts, described, for example, in *Remington's Pharmaceutical Sciences,* (Gennaro, A., ed.), Mack Pub, (64).

The invention also includes the use of these pharmaceutical compositions for the above-described methods, e.g. to enhance platelet adhesion, aggregation, improve clotting efficiency and shorten bleeding time in a variety of diseases and disorders, including, but not limited to, immune or idiopathic thrombocytopenic purpura, drug- and chemotherapy-induced thrombocytopenia and other thrombocytopenias, von Willebrand disease, hemophilia and other bleeding disorders.

A mammal in need of treatment may be suffering from inherited or acquired coagulation or platelet disorders. Thrombocytopenias of various causes such as idiopathic thrombocytopenic purpura, therapeutic or accidental exposure to cytotoxic agents causing thrombocytopenia (e.g. cancer chemotherapy), or impaired platelet functions caused by drugs or systemic illness or congenital or acquired forms. Coagulation disorders include vWd, hemophilias and other clotting factor deficiencies. Other disorders of hemostasis, not well defined, such as disorders of blood vessels, can be benefited by the invention. The microparticles described herein, such as EMP, PMP, RMP and LMP will enhance coagulation and hemostasis, thereby alleviating excessive bleeding. Effective dosages of microparticles can be determined without undue experimentation by those of skill in the art and are generally expected to be between $10^6$ and $10^{12}$/kg, more usually between $10^8$ and $10^{10}$/kg.

EMP, RMP and other microparticles may be administered in any suitable pharmaceutical composition according to the pharmaceutical arts, including phosphate buffered saline (PBS) or other physiologically acceptable buffers known to those of skill in the art, and optionally with additional therapeutic compounds, excipients and carriers as may be considered advantageous. pH of the buffer should generally be equal to or below 7.4.

Although the utility of the present invention is not dependent upon any theory, the inventors believe that EMP released during vascular injury may help stop bleeding by rapidly interacting with clotting factors and/or platelets via membrane-associated vWf multimers and adhesins to stabilize platelet aggregates in the local microenvironment and RMP released from red cells may provide clotting factors such as tissue factor and phospholipid surfaces to promote blood clot formation.

It has been found that the use of RMP can be particularly advantageous. In one embodiment, an individual's own red cells are used to produce RMP to be administered to that individual. Since red cells are abundant, a small portion of red cells will be collected safely from, for example, a patient in need of treatment of a bleeding disorder, or those undergoing surgeries or injured by trauma, RMP will be produced to be used for treatment and to reduce blood loss. RMP may express TF and/or FVIII naturally or RMP may be treated ex vivo to express or deliver such factors. A method of preparing RMP for treatment of bleeding disorders is described herein below. In one embodiment of the invention, TF-expressing RMP can be used as the basic or universal hemostatic agent in prevention of bleeding in patients with bleeding disorders or anyone at risk of bleeding, such as patients in surgery, traumatic injury or certain invasive diagnostic or therapeutic procedures such as cardiac catheterization, bronchoscopy, colonoscopy and endoscopy, pleural or spinal tap, arteriogram, venogram and various biopsy procedures etc for diagnostic purpose as well as insertion of IV or central lines or special catheter insertion for dialysis, stents for heart or other organs, plasmapheresis, stem cell collection etc for therapeutic purpose.

RMP generated by sonication or other methods appear hemostatically active and useful for the purpose of reducing bleeding. But in certain conditions, additional measures to improve its efficacy may be needed. As required, RMP may be modified to render them more effective, termed hemostatically modified RMP (hmRMP). hmRMP can also be transfused into patients to reduce blood loss or treat bleeding conditions. The use of RMP compared to other conventional therapies will eliminate blood-borne infections such as HIV, hepatitis etc. enhancing patient safety. It will also eliminate the risk of autoimmune reaction to synthetic or foreign materials, which may occur when synthetic vesicles, etc. are used, and thereby eliminates the risk of autoimmune diseases as long term complications. In addition, the preparation of RMP is far less expensive than preparing other cell derived microparticles or synthetic membrane vesicles. Thus, this novel approach of using RMP obtained from individual's own blood to treat their anticipated or active bleeding complications will eliminate common, serious potential side effects of blood transfusion or infusion of foreign materials.

Addition augmentation may be made to the MP, in particular RMP. For example, tissue factor (TF), fibrinogen, RDG peptide or other adhesins can be attached to RMP. Many recombinant or chemically purified products, essentially free of blood-borne infectious agents, are available and may be used for this purpose. Methods of conjugation of specific proteins or peptides to phospholipids (PL) vesicles are well-known in the art, see in particular the comprehensive text by Greg T. Hermanson, *Bioconjugate Techniques* (54). Cell derived microparticles are essentially PL vesicles, it is reasonably expected that the same methods are applicable.

Specific patients suffering from a particular factor insufficiency may be treated with MP conjugated to that factor to correct or ameliorate that particular bleeding disorder. For example, patients with hemophilia may be treated with MP conjugated to FVIII, using MP generated from their own red blood cells (autologous RMP). Similarly, vWF can be conjugated to RMP in treating those with von Willebrand disease. Recombinant or purified products free of blood borne infectious agents are available for conjugation to MP or RMP for hemostatically modified MP or RMP (hmRMP).

RMP therapy will reduce or eliminate need of allogeneic blood transfusion in many patients. By reducing the need for repeated or severe blood transfusion, this therapy will substantially ease shortages in blood supply, an increasingly critical problem in medicine.

Individuals who may benefit from RMP and hmRMP or other MPs and their chemically modified variants include patients with various blood clotting disorders, platelet disorders such as thrombocytopenia or platelet dysfunctions as well as ill-defined bleeding disorders and bleeding disorders caused by problems in blood vessel wall. In addition, individuals who must undergo major surgery or invasive diagnostic procedures in which bleeding is often a complication, or individuals otherwise expecting significant blood loss, can benefit by infusion of RMP or hmRMP. Benefit may be derived either from MP preparation of the patient's own blood, if time permits, or derived from RMP or hmRMP derived from donor blood. Furthermore, individuals who are prone to injury or trauma can benefit from prior infusion of their own RMP (e.g. individuals with balance problems, and those who participate in activities where physical trauma is a risk, such as hockey players, prize-fighters, etc). RMP therapy will also benefit patients undergoing chemotherapy or any medical therapy that predisposes a patient to increased bleeding risk, patients who develop coagulopathy or platelet dysfunction or other bleeding conditions associated with medical or surgical therapy, patients having bleeding complications from overdoses of medications such as Coumadin or other blood thinners or antiplatelet drugs to prevent blood clots, and patients with chronic diseases that predispose to increased bleeding risk such as chronic renal failure, chronic liver diseases or any other diseases that increased bleeding risks.

RMP, EMP and other MPs can be stored (e.g. as components in kits) and used when needed by those who are prone to bleed or expecting procedures that cause significant bleeding.

It is a further embodiment of the invention that in certain clinical settings, it may be necessary to give combined MPs. For example, EMP administered first, then RMP infused later or given simultaneously.

As used herein, an "excessive bleeding condition" is any condition that causes or may cause bleeding to be prolonged or in excess of normal. Such conditions include, but are not limited to, clinical bleeding disorders such as idiopathic thrombocytopenic purpura, drug or chemotherapy-induced thrombocytopenia, thrombocytopenias of various causes, both congenital or acquired or platelet dysfunctions from various causes, both congenital and acquired or coagulation disorders including von Willebrand's disease or hemophilia or other clotting disorders, both congenital and acquired, physical trauma, invasive diagnostic procedures and surgery.

This application claims priority to U.S. provisional application No. 60/633,417, which is hereby incorporated by reference.

BRIEF DESCRIPTION OF THE DRAWINGS

FIG. 8. Effect of Endothelial Microparticles on the Hemostatic Activity in an In Vivo Thrombocytopenia Model. Adult Fischer rats were administered a single dose of cyclophosphamide (CTX, 75 mg/kg) intraperitoneally to induce thrombocytopenia, and challenged after 4-5 days by tail clipping. Results show bleeding time in control, CTX treated, and CTX+EMP treated animals.

FIG. 11. Procoagulant activity of RMP and LMP in vitro. RMP or LMP at $1\times10^8$ were added to PRP in the presence of corn trypsin inhibitor (1 U/mL), then calcium (10 mM) was added to initiate clotting process. The results showed that RMP are more potent than LMP in promoting clot formation.

FIG. 12. Hemostatic activity of RMP in vivo. Three adult Fischer rats were administered a single dose of cyclophosphamide (CTX, 75 mg/kg) intraperitoneally to induce thrombocytopenia (low platelet count), then tested for bleeding time after 4-5 days by tail clipping. As shown, treating with CTX result in prolonged bleeding time (760 sec) as compared to 60 sec of the control (CTX-untreated) rat. When CTX-treated rats were infused with two doses of RMP at $1\times10^7$ and $1\times10^8$, their bleeding times were shortened dramatically. At higher dose ($1\times10^8$), the bleeding time was shortened to 220 sec.

DETAILED DESCRIPTION

We have previously shown that vWf is bound to subspecies of EMP (32), but the functional significance was not known. The results described hereinbelow demonstrate that platelet-EMP interaction is mediated through vWf, and compare the stability of the platelet aggregates formed by EMP to those formed by normal plasma, Humate-P, and TTP plasma. In addition, we studied the effect of vWf-positive EMP on the ristocetin-induced aggregability of plasma from patients with von Willebrand disease (vWd). Further, we have compared and correlated the size of the vWf multimers between EMP-bound vWf vs. soluble vWf from normal and TTP plasma, and Humate-P with the stability of the platelet aggregates. Additionally, we present results from two patients with severe ITP correlating high levels of RMP with a reduced number of bleeding episodes compared to the average population of ITP patients, and in vitro laboratory data demonstrating that RMP are effective hemostatic agents.

Methods and Materials

Materials

Human cultured endothelial cells of renal or brain, and coronary artery origin were obtained from Cell Systems (Kirkland, Wash.). FITC-labeled anti-CD62E (clone 1.2B6, Cat. # F-0674) was obtained from Sigma (St. Louis, Mo.). Anti-CD42b (clone SZ2, Cat. # IM0409) and CD41(Cat. #IM0649) were obtained from Beckman-Coulter (Miami, Fla.). HRP-conjugated anti-vWf (Cat # AHP 062-P) was purchased from Serotec Inc. (Raleigh, N.C.). Gel electrophoresis reagents and instruments were obtained from Bio-Rad (Richmond, Calif.). Ristocetin (Sigma, St. Louis, Mo.) was purchased from Chrono-Log. Humate-P®, a therapeutic reagent containing concentrated Factor VIII and vWf multimers, was obtained from Aventis-Behring (Marburg, Germany). Other chemicals were purchased from Sigma (St. Louis, Mo.).

Preparation of EMP and platelets Human Cultured Endothelial Cells (EC) of Renal, Brain, or coronary origin were activated with TNF-α (10 ng/mL) for 24 hr to induce EMP generation (13). The culture supernatants were then centrifuged at 15,000×g for 30 min to sediment EMP, which were then washed 3× with PBS buffer and re-suspended in PBS to 1/10 original volume. Concentration of EMP was measured by flow cytometry using FITC-labeled anti-CD62E as described by Jimenez et al. (33).

Washed platelets were prepared by centrifuging platelet-rich plasma (PRP) at 600 g for 10 min in the presence of 10 mM of EGTA and 1 μM of $PGE_1$. The pellets were washed twice with PBS, and then suspended in PBS at $1×10^8$/mL.

Assay of EMP-platelet interaction and ristocetin-dependent aggregation by flow cytometry. EMP at $5-100×10^6$/mL final concentration were incubated with normal washed platelets at $1×10^7$/mL final, in the presence or absence of ristocetin (1 mg/mL) for 10 min with gentle orbital shaking (100 rpm). Binding of EMP to platelets was assessed by co-expression of EMP marker CD62E with platelet marker CD41 in flow cytometry. In those experiments, plasma was used from 1% to 15% as indicated; and Humate-P from 0.02 to 0.4 U/mL as indicated. Platelet aggregation was measured by flow cytometry (34) by counting the number of free platelets (<5 um) shifted to a bit-map representing platelet aggregates (>5 um). The flow rate of the Coulter XL flow cytometer was at medium setting and discriminator was forward scatter (FS), level 3. The number of platelets was calibrated with standard beads with known concentrations. A decrease in singular free platelets (accompanied by increase in number of platelet aggregates) was observed when ristocetin was present in the plasma. At maximal plasma or Humate-P plus ristocetin (1 mg/mL), only <5% of platelets remain singular (free). Reduction of number of singular platelets with and without ristocetin was measured as an indicator of platelet aggregate formation rather than counting the number of micro-aggregates because the latter is ambiguous owing to heterogeneous size distribution and sticking to the flow chamber and tubing.

Dissociation of ristocetin-induced platelet aggregates After 20 minutes of platelet aggregate formation at room temperature, the samples were diluted with PBS (1:20 volume ratio) to induce a time-dependent dissociation. Increases of free platelet counts after dilution were monitored at intervals to determine the time-course of dissociation of platelet aggregates by flow cytometry.

vWf multimer analysis. The method of Raines, et al. (36) was employed with minor modifications as follows. Cooling during electrophoresis was accomplished by resting the horizontal gel electrophoresis apparatus on an aluminum block immersed in ice-water slurry and the buffer chambers were also on ice. Several agarose gel concentrations were tested and 0.8% was found to be optimal for showing a wide range of multimer sizes. Western blotting was according to Raines et al except that the anti-vWf was pre-conjugated with HRP (Serotec Inc., Raleigh, N.C.; Cat # AHP 062-P) and was used at 1:500 dilution (50 uL in 25 mL). The proteins in the gel were transferred into PVDF membrane by capillary diffusion with layers of paper towels on top of PVDF membrane overnight with PBS as transfer buffer. The PVDF membrane was then blocked with 0.5% casein solution. Staining of the PVDF membrane was accomplished by the method of Nakane (37) using dye 4-chloro-1-napthol (4CN; Sigma, Cat. #C-8890) prepared fresh by dissolving 30 mg in 5 mL of ethanol, then bringing to volume 100 mL by adding 50 mM Tris buffer pH 7.6 containing 0.03% $H_2O_2$ (1 mL of 3% $H_2O_2$ in 100 mL).

Clinical studies. For Examples 4-6, citrated blood was obtained from four TTP and four Type I vWd patients. The four TTP patients all presented with the classic triad of TTP; severe thrombocytopenia (platelet count $<2×10^7$/mL), microangiopathic hemolytic anemia, and mental dysfunction. The type I vWd patients were characterized by low vWf total antigen and deficient ristocetin cofactor activity. The protocol was approved by the Institutional Review Board, and informed consent was obtained from the patients.

For Example 8, blood (citrated to optimize preservation) was obtained from atypical ("nonbleeding") ITP patients, characterized in standard clinical studies, and compared to normal controls and typical ITP patients.

Statistical Analysis. For comparing three or more groups, one way ANOVA was use to determine the p values. If p<0.05, then two tailed Student's t test was used to analyze the significance (p<0.05) of difference between the means of two groups. In cases where the data failed the normality test, then the Mann-Whitney rank sum test was used. All data analyses were performed using Windows-based program, Statmost.

Methods for Microparticle Production.

I. Platelet Microparticles.

Platelet microparticles may be prepared by at least three different methods, as indicated below, and as are well known to one of skill in the art.

1) Blood-bank source. Stored platelets release abundant PMP with time (see section 4.5, "*Platelet Storage Lesion*," of reference 1) This method may be utilized to make use of platelet concentrates that have been expired by up to 5 days, which are normally discarded.

Procedure: Platelets expired by 1-5 days are sedimented by centrifugation 10 min at 200×g, room temperature, sterile. Observing sterile technique, the supernatant is diluted to double volume by adding PBS/citrate, then the microparticles are sedimented by centrifuging 8,000×g for 30 min. The resuspended PMP may be refrigerated for storage, then re-washed prior to use. Resuspend in desired i.v. medium (e.g. saline).

2) Ultrasonic method. PMP may be obtained in high yield by sonic disruption.

Procedure: Fresh (or recently expired) platelets at physiologic concentration ($2.5×10^5$/uL), previously washed 2× in PBS buffer with 1 mM EDTA/5 mM $MgSO_4$ (to minimize aggregation), are exposed to ultrasonic disruption [Branson Instruments; 5 mm titanium probe] in a 50 mL polypropylene tube for 3-5 bursts of 3-5 seconds each at room temperature. Residual platelets and debris are removed by centrifugation and the PMP in the supernatant are sedimented by high-speed spin, then washed as above.

Sterile technique adequate for animal studies consists of a cotton plug in a hole drilled in the cap of the tube sufficient to admit the sonic probe, which is wiped with alcohol swab prior to inserting through the sterile cotton collar. For human use, appropriate sterile techniques are known to those of skill in the art.

3) Calcium activation method. In normal physiology, a rise in cytosolic calcium is the final common step of all pathways leading to cell activation. Use of reagent calcium ionophore, such as A23187, creates a pore in the membrane which selectively admits calcium from the external medium, causing abundant PMP release. The resulting may be more physiologically relevant.

Procedure. The method of Arnout et al (42) can be used to prepare PMP, and the resulting PMP express significant vWf by electrophoresis/blotting [unpublished]. Briefly, 1.0 mL washed platelets are suspended at $2.5 \times 10^5$/uL in HEPES/saline pH 7.4, then ionophore A23187 sufficient to make 1 umol/L final is added (prediluted from alcohol stock solution) in 50 uL buffer, sufficient calcium to make 2 mM final, then gently agitate for twenty minutes at room temperature. Centrifuge to remove heavy debris, and recover PMP from supernatant as above. Alternate: Platelets may be permeabilized with saponin instead of ionophore if there is any concern that ionophore will persist in the PMP; then proceed as above. Alternate: Platelets may also be activated with thrombin+ collagen, reported to have potency similar to ionophore activation.

II. Erythrocyte (Red Cell) Derived Microparticles (RMP)

As described in I (1) above, patients' own blood or blood-bank blood is also known to naturally shed abundant RMP. Therefore, they may be harvested exactly as described in I (1). Fresh RBC as described in I (2-4) as well as stored RBC can be used for generation of RMP.

III. Synthetic Microparticles

Liposome approach (Synthetic MP). On the assumption that vWf in conjunction with procoagulant phospholipids (PL) are by themselves sufficient to afford significant hemostatic protection in thrombocytopenic patients, vWf-cephalin (or lecithin) liposomes should be efficacious. The experience of the inventors shows that both soybean and egg lecithin are almost as active in coagulation assays (tissue factor, also lupus anticoagulant) as is cephalin, the crude brain lipid traditionally used for this purpose. The substantial advantage of this approach is limited immunogenic proteins, other than vWf itself.

Procedure: Briefly, vWf concentrate (such as Humate P® or equivalent prepared in-house from plasma) is exposed to ultrasonic energy in the presence of liposomes of cephalin or lecithin, in concentrations well known in the art. Under appropriate conditions, essentially all of the vWf becomes tightly associated with the liposomes, either on the surface or transmembranally. Optimum conditions can be determined by those of skill in the art without undue experimentation.

EXAMPLES

Example 1

Figure 1:
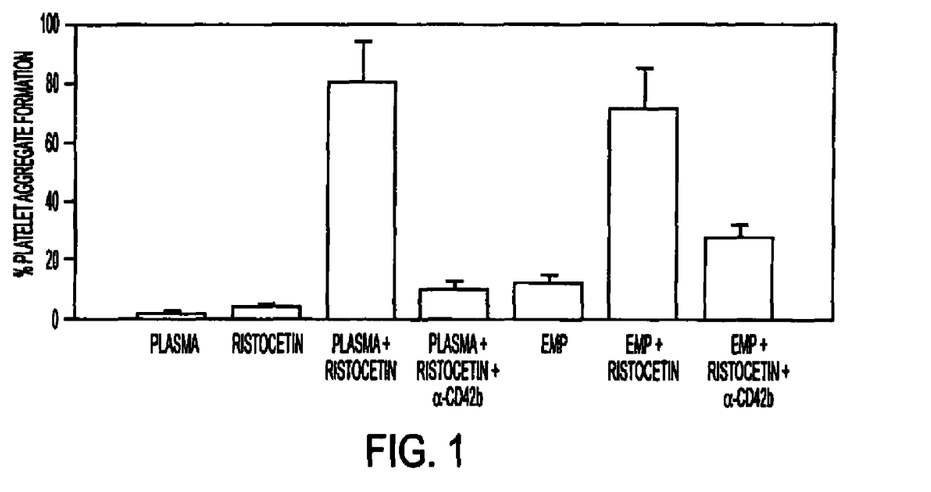
FIG. 1. Comparison of EMP-induced platelet aggregate formation in the presence or absence of ristocetin. In the presence of ristocetin (1 mg/mL), renal EMP ($4 \times 10^7$/mL) induced strong platelet aggregation similar to that induced by 8% plasma. Both EMP- and plasma-induced platelet aggregations were inhibited by a blocking anti-CD42b mAb (CD42b is the receptor binding site for von Willebrand factor (vWf) and thrombin located on platelets). In contrast, EMP induced little platelet aggregation in the absence of ristocetin. N=5; mean ±S.D. * indicates p<0.01 comparing between the "plasma+ristocetin+α-CD42b" group and the "plasma+ristocetin" group, and ** indicates p<0.03 comparing between the "EMP+ristocetin+α-CD42b" group and the "EMP+ristocetin" group.

Platelet aggregation induced by EMP. EMP were incubated with normal washed platelets as described above. The presence of EMP at $4 \times 10^7$/mL final induced strong platelet aggregation which was dependent on ristocetin. As seen in FIG. 1, the degree of ristocetin-dependent platelet aggregation caused by EMP was similar to that caused by 8% normal plasma. In the absence of ristocetin, negligible platelet aggregates were formed with either EMP, Humate-P, or normal plasma. Both EMP-induced and plasma-induced platelet aggregation was inhibited by anti-CD42b blocking mAb. These results demonstrate that EMP induced platelet aggregate formation that is vWf-dependent.

Figure 2A:
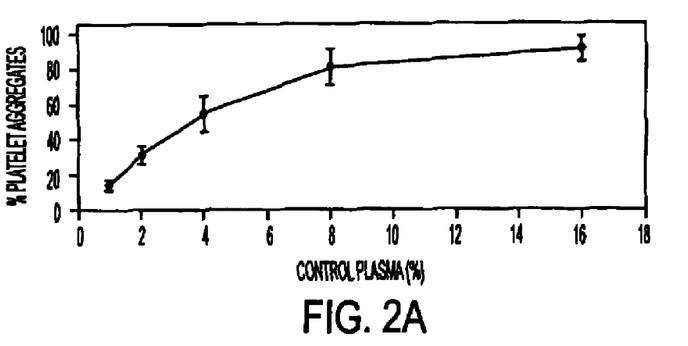
FIG. 2. Dose response curves of platelet aggregate formation induced by plasma, Humate-P or EMP in the presence of ristocetin. The dose response curves of renal EMP/ristocetin-induced platelet aggregation showed that vWf cofactor activity of $1\times10^7$ EMP/mL is equivalent to 3.5% plasma or 0.075 U/mL of Humate-P. N=5; mean ±S.D.
Figure 2B:
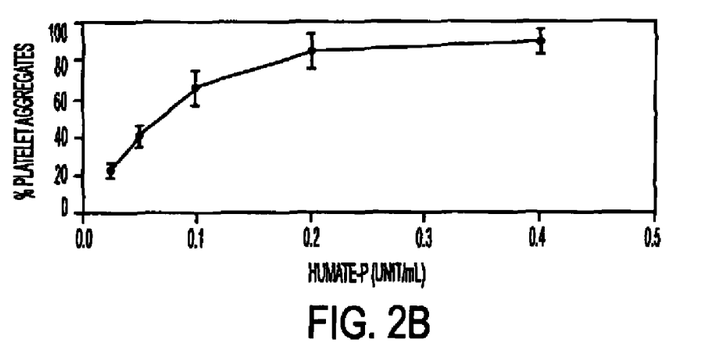
Figure 2C:
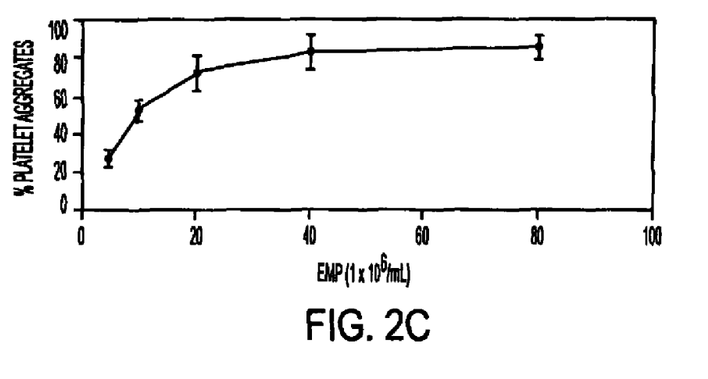

The dose-response curves of platelet aggregation induced by EMP, normal plasma, or Humate-P are shown in FIG. 2. It is noted that the shapes of the curves for all three agents are similar. Since both the platelets and the EMP were prewashed and essentially plasma-free, these results demonstrate that EMP-bound vWf can substitute for soluble vWf in plasma or Humate-P in inducing full platelet aggregation with ristocetin. The data indicate that 50% aggregation occurs with 3.5% plasma, equivalent to $1 \times 10^7$/mL of EMP, and to 0.075 U/mL of Humate-P.

Figure 3:
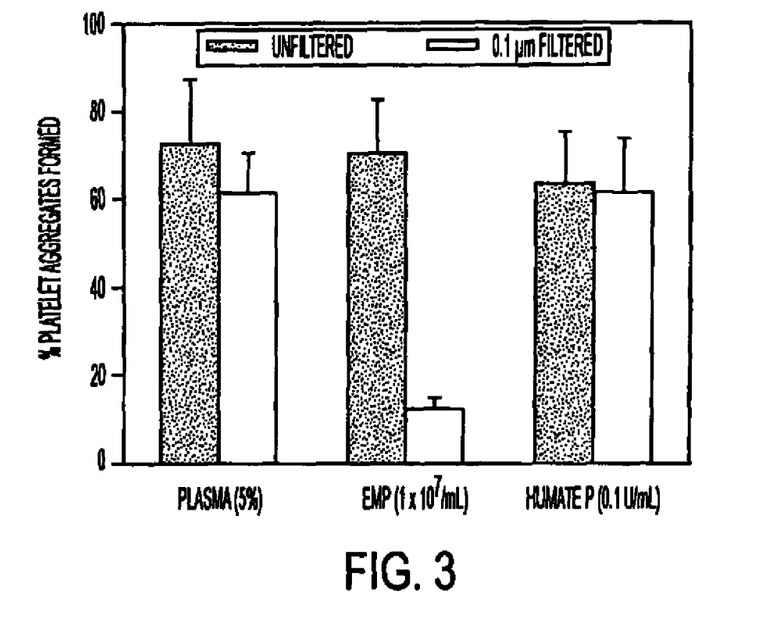
FIG. 3. Effects of 0.1 μm filtration on plasma-, Humate-P-, or EMP-induced platelet aggregate formation in the presence of ristocetin. Filtration through 0.1 μm filter largely abolished renal EMP-induced platelet aggregation but had little or no effect on plasma or Humate-P induced platelet aggregation. N=4; mean±S.D. * indicates p<0.01 comparing between "filtered EMP" group and the "unfiltered EMP" group.

To further confirm the existence of microparticle-bound vWf, we tested the effect of filtration through 0.1 μm filter, which is known to retain the majority of EMP. As shown in FIG. 3, this filtration largely abolished EMP-induced platelet aggregation but had no significant effect on normal plasma- or Humate-P-induced platelet aggregation.

TABLE 1

Comparison of vWf activity of EMP derived from different sources of human tissue cultures.

| | Subtypes of EMP | | |
|---|---|---|---|
| | Renal | Brain | Coronary |
| % Platelet aggregates induced by $2 \times 10^7$/mL EMP | 68 ± 13% * | 54 ± 10% * | 29 ± 6% |

Example 2

EMP from endothelia of different origins. We compared aggregation activity of EMP from three different sources of EC: microvascular renal and brain, and macrovascular coronary artery. All three EC were cultured under conditions similar to those detailed previously (13, 33, 34) and were stimulated with the same concentration of TNF-α for 24 hr. EMP were collected and washed as described above, counted by flow cytometry, and adjusted to equal concentrations. Table 1 shows the relative specific activities of the EMP from these three sources in inducing vWf-dependent platelet aggregation with ristocetin. It is seen that EMP derived from renal or brain microvascular EC were more potent than those from coronary artery EC. This is consistent with our previous findings that renal or brain EMP contained higher percentage of vWf+EMP (33) and with the fact that the clinical manifestations of abnormally active vWf are mainly related to microangiopathic thrombosis.

EMP obtained from renal, brain and coronary artery endothelial cells (EC) as described in the "Methods" section were adjusted to equal concentrations prior to evaluating their pro-aggregatory activity in the presence of ristocetin. The table shows that EMP from different EC lines exhibited different activities in ristocetin-induced platelet aggregation, in the following order, renal>brain>>coronary EC.N=4, mean±S.D. * indicates p<0.01 as the "renal EMP" or "brain EMP" group compared to the "coronary EMP" group.

Example 3

Figure 4:
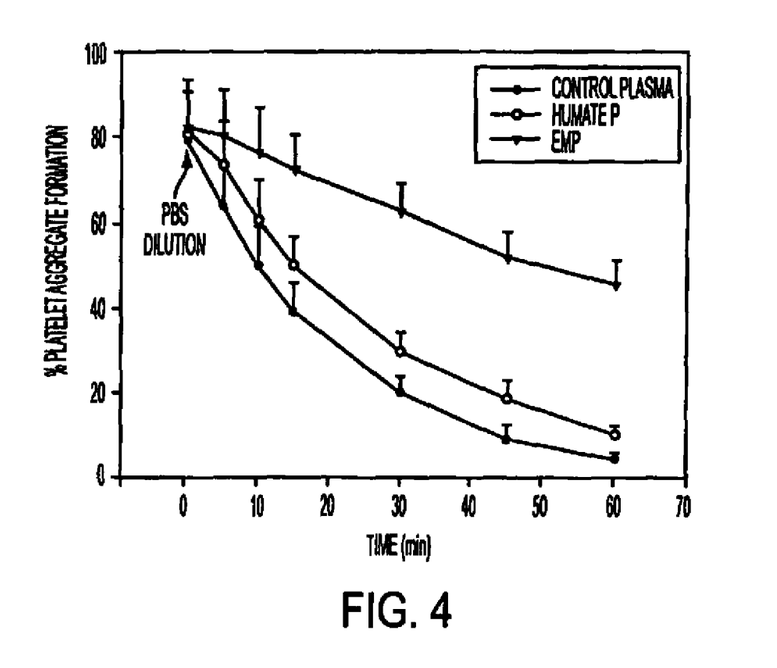
FIG. 4. Time course of dissociation of platelet aggregates formed by plasma or EMP. After platelet aggregates were induced for 20 min, the mixtures were diluted with phosphate buffed saline (PBS) (1:20) to initiate dissociation of aggregates. At intervals, samples were assayed for increases of free platelets as measured by flow cytometry. The time of 50% dissociation for plasma, Humate-P, and EMP was 15, 25, and 60 min respectively. N=4; mean±S.D.

Assessment of aggregate stability. In the course of pilot studies, we observed that when platelet aggregates induced by plasma plus ristocetin were diluted 20-fold with PBS buffer, the aggregate population gradually decreased and the number of free platelets increased in a time-dependent manner. FIG. 4 depicts the time course of dissociation of platelet aggregates induced by plasma, Humate-P, and EMP. After platelet aggregates were induced for 10 min, the mixtures were diluted with PBS (1:20) to initiate dissociation. The time for 50% dissociation for plasma, Humate-P and EMP were about 15, 25 and 60 minutes respectively. These results demonstrate that platelet aggregates induced by EMP are more stable than those induced by plasma or Humate-P. We postulated that the greater stability of the aggregates formed by EMP may be due to (i) the presence of very large multimers of vWf on EMP and/or (ii) the presence of other adhesion molecules contributing to cross-linking between EMP and platelets.

Example 4

Effects of TTP plasma on ristocetin induced platelet aggregate formation. Because abnormal degree of vWf multimerization has been implicated in TTP (37,38), we investigated plasmas from four TTP patients in acute (A) and remission (R) phases, compared to normal pooled plasma. As shown in Table 2, TTP patients exhibited significantly increased ristocetin-induced platelet aggregation, in both acute and remission states.

TABLE 2

Comparison of vWf actvity of plasma from TTP in acute and remission phases with control.

| | Sources of plaasma | | |
| --- | --- | --- | --- |
| | Control | TTP-A | TTP-R |
| % platelet aggregates induced by 4% plasma | 45 ± 6% (N = 8) | 79 ± 16% * (N = 4) | 70 ± 12% * (N = 4) |

PPP (4%) from four different TTP patients in acute (A) and remission (R) phases and pooled control plasma were incubated with platelets and ristocetin for 10 min, then the remaining free platelets were assayed by flow cytometry. The platelet aggregate formation by TTP plasma in acute or remission phase was compared to the control group, mean ±S.D. * indicates p<0.05 comparing TTP in acute phase or TTP in remission phase vs. the "control" group.

Figure 5:
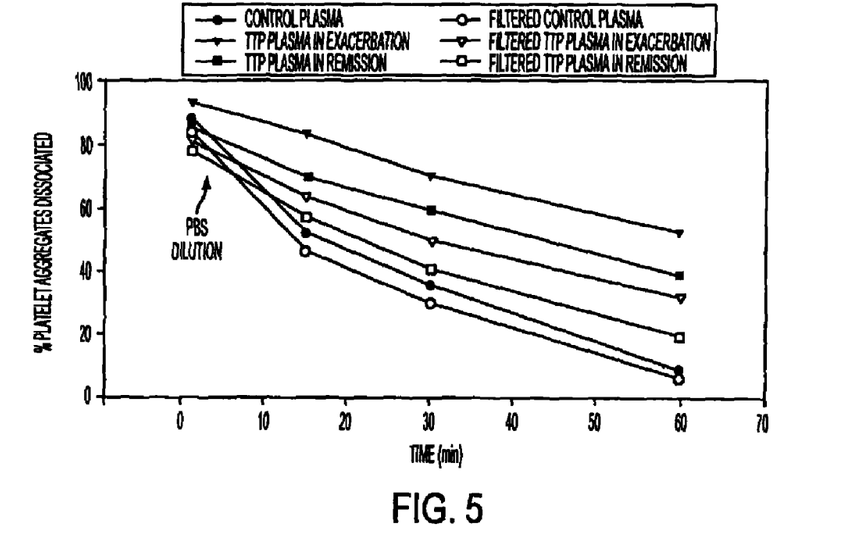
FIG. 5. Platelet aggregates induced by thrombotic thrombocytopenic purpura (TTP) plasma or EMP are more resistant to dissociation than those induced by normal plasma with or without 0.1 μm filtration. Four percent of PPP from four different TTP patients at acute phases and control plasma were incubated with platelets and ristocetin for 20 min, then the samples were diluted with large volume of PBS (1:20) to initiate dissociation of aggregates as described in FIG. 5. This figure shows that Platelet aggregates induced by TTP plasma or EMP are more resistant to dissociation than those induced by normal plasma. Filtration of TTP plasma resulted in about 20-30% loss of aggregate dissociation. For controls, each data point is the mean of 6 samples. For TTP plasma, each data point is the mean of 4 different samples.

The platelet aggregates produced by TTP plasma were also markedly more stable than with normal plasma. As shown in FIG. 5, the platelet aggregates with TTP plasma were much more resistant to dissociation after 1:20 dilution than normal plasma, and this was seen in both acute (exacerbation) and remission phases. Filtration of the TTP plasma through 0.1 um to remove MP of size ≧0.1 um facilitated dissociation partially. The time course of dissociation with TTP plasma of acute phase plasma was similar to that of EMP (FIG. 4). These results indicate that EMP-bound vWf in TTP plasma may contribute in part to stabilizing platelet aggregates.

Example 5

Figure 6:
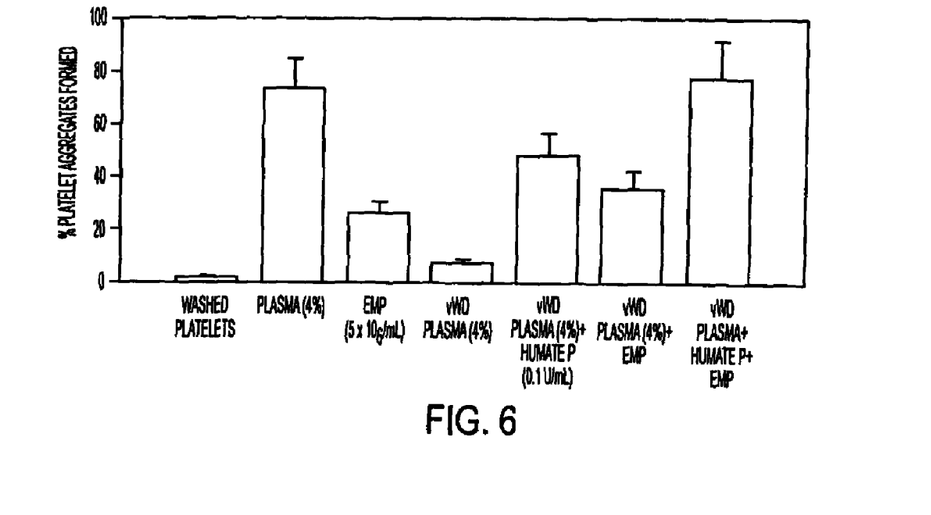
FIG. 6. Addition of EMP to vWd plasma rescued the platelet aggregation activity of vWd plasma. Addition of EMP or Humate-P to vWd plasma restored the platelet aggregation activity of vWd plasma. A synergistic effect was achieved by combining low concentration of EMP ($5\times10^6$/mL) with low dose of Humate-P (0.1 U/mL). N=4; mean±S.D.

Application of EMP-bound vWf to vWd plasma As shown in FIG. 6, plasma from four vWd patients was used to evaluate their vWf-dependent platelet aggregating activities. Plasma from vWd patients showed very weak platelet aggregating activity. However, this activity increased dramatically after addition of Humate-P (0.1 U/mL, final conc.). The figure also shows that addition of EMP ($5\times10^6$/mL, final conc.) to the vWd patient plasma in vitro restored partially the aggregation activity of the vWd plasma. A synergistic effect of EMP and Humate-P combined induces strong platelet aggregate formation.

Example 6

Figure 7:
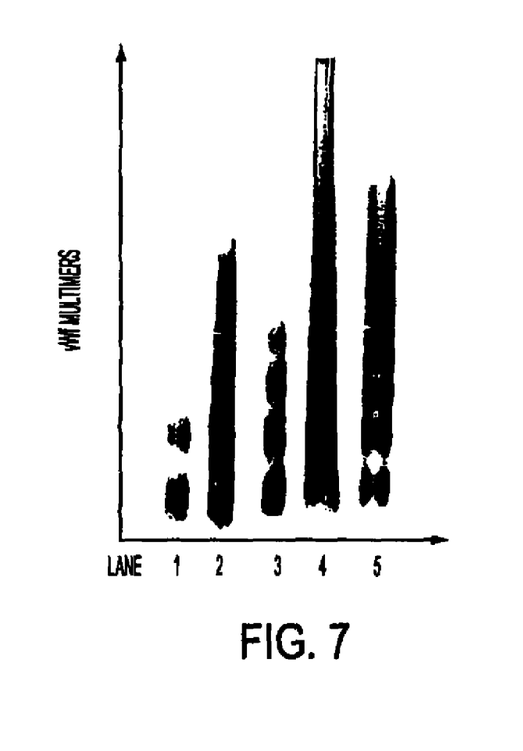
FIG. 7. Analysis of vWf multimers from different sources by 0.8% agarose gel electrophoresis and Western blotting. Lane 1, plasma from a Type I vWd patient (5 μL); Lane 2, plasma from a TTP patient in acute phase (5 μL); Lane 3, plasma from a normal control (5 μL); Lane 4, renal EMP ($2\times10^7$ counts); Lane 5, diluted Humate-P (0.01 U).

Multimer analysis of EMP-bound vWf compared to vWf from normal plasma TTP plasma, and Humate-P. We postulated that the observed effects of EMP on ristocetin-induced platelet aggregation could be due to the presence of unusually large vWf multimers (ULvWf) on EMP. As shown in FIG. 7, multimer analysis confirms that EMP-bound vWf multimers (Lane 4) are larger than those from normal plasma (Lane 3), and even larger than those from Humate-P (Lane 5), or plasma from a TTP patients whose plasma exhibited ULvWf (Lane 2). We also noticed that vWf multimers from a vWd Type I patient contain very few bands (Lane 1). We have noticed that the vWf multimer bands from EMP sample are not clearly separated from each other as observed with soluble vWf. One possible explanation for this is that membrane bound vWf multimers may be tightly bound with certain membrane phospholipids that are not fully dissociated by SDS, which may cause more diffuse bands.

Example 7

Figure 8:
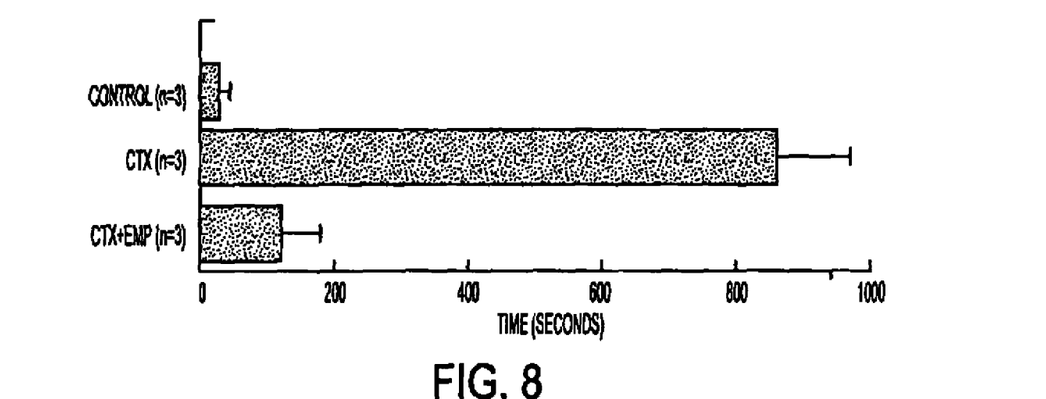

Use of EMP composition to decrease bleeding time in vivo. In order to demonstrate in vivo efficacy of the EMP, adult Fischer rats were divided into three groups. Group 1 served as normal controls. Groups 2 and 3 were injected intraperitoneally with a single dose of cyclophosphamide (CTX, 75 mg/kg) to induce thrombocytopenia. After 4-5 days, when the platelet count was reduced to less than $5\times10^5$/μL in the treated groups, the bleeding time was measured by clipping the tail 2 mm from the tip under anesthesia. Prior to testing, group 3 was injected intravenously with $2\times10^8$ EMP in 0.5 ml PBS two minutes prior to tail clipping. As shown in FIG. 8, in normal controls, bleeding time was less than one minute. Group 2, which received CTX only, had an average bleeding time of more than 800 seconds. Group 3, which received CTX+EMP, had a greatly reduced bleeding time (less than 200 seconds) compared to Group 2. These results demonstrate the hemostatic potency of EMP in vivo.

Example 8

Figure 9:
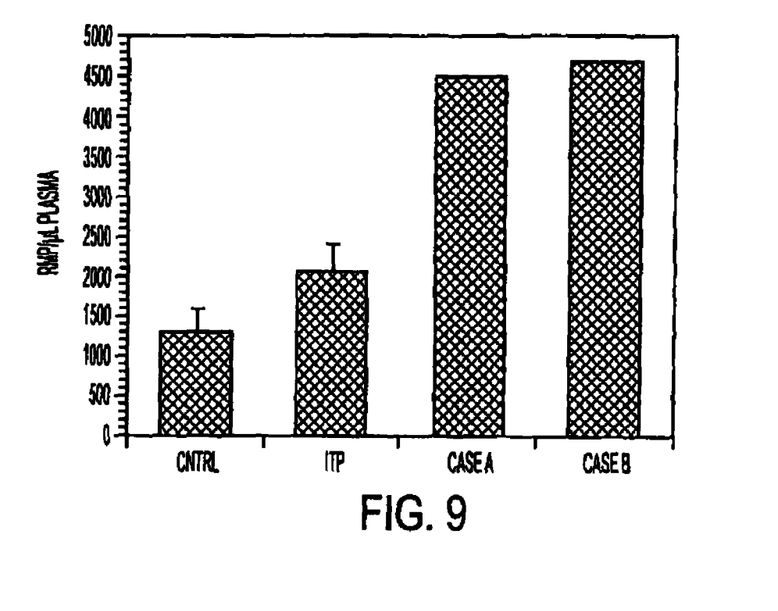
FIG. 9. Clinical laboratory studies comparing RMP in classical ITP patients with those (See case studies patient A and B in the text) with long-term freedom from bleeding. Data on two ITP patients (Case A and B) with severe ITP (platelet counts 10,000 or less) who have shown little bleeding over 30 years were compared to those of typical ITP patients, manifesting usual bleeding symptoms and with healthy controls. PMP, EMP, LMP, coagulation tests and blood chemistries were similar among all ITP patients, including Case A and B. The only distinction of Cases A and B was exceptionally high RMP.

Clinical observations on atypical non bleeding ITP patients. We have recently observed a limited number of ITP patients who are highly unusual in their absence of bleeding symptoms (asymptomatic) in spite of severe thrombocytopenias. Their platelet counts were 10.000 or less in most of time in their clinical courses of ITP over 30 years but they never experienced major bleeding and enjoy fairly normal life. Investigation on these patients revealed that exhibit exceptionally high levels of RMP (two shown, A, B). See FIG. 9. They exhibit no other abnormal feature to account for absence of bleeding. We attribute their asymptomatic features to the protective effect of their high RMP, as also supported by data below.

Two patients were identified with severe ITP (platelet counts 10,000 or less) who nevertheless lived normally for over 40 years, with not a single episode of major bleeding. Careful studies of these patients revealed that both had extremely high levels of red cell microparticles (RMP), compared to other ITP patients who tend to bleed (49,50). (See FIG. 9). Clinical observation on these two patients (case studies A and B below) suggested to us that RMP are hemostatically active and that the high level of RMP could account for the unusual absence of bleeding in these patients.

Case study (A). Patient A developed ITP at age 4 yr, when her mother noted easy bruising. Upon subsequent evaluation a diagnosis of ITP was made. She underwent splenectomy after alternative therapies failed. Remission after splenectomy lasted one year; ITP relapsed shortly after polio vaccination. Her ITP responded only transiently to high dose glucocorticoids, IV gammaglobulin and not at all to other measures (vinca alkaloids, danazol, colchicines, Prosorba column, WinRho, etc.). Over the course of 47 yr of chronic ITP, her platelets stayed around 10,000/uL. She manifested bruises upon minor trauma, occasionally petechiae, but seldom suffered from mucosal bleeding and never experienced a major bleeding event requiring blood transfusion. She experienced heavy menstrual bleeding temporarily requiring prescription of birth control pills, which controlled the bleeding. She now lives a normal life as an active wife and mother. She also suffered frequent migraines requiring frequent parenteral pain medication. Because of severe thrombocytopenia, multiple CAT scans and MRI were performed for fear of CNS bleeding but were negative. She never had this complication.

Clinical results: Platelets 7,000/uL, hemoglobin 13.3, hematocrit 39.1%, WBC 9.3 with normal differential. Blood chemistries including LDH were all normal. PT, aPTT and other coagulation tests were all within normal limits. ANA, C3, C4 were normal. Antiphospholipid antibodies and lupus anticoagulant were negative.

Antibodies against platelet glycoprotein IIb/IIIa and Ib/IX, measured by platelet associated IgG characterization assays, "PAICA" (52), were strongly positive, supporting diagnosis of ITP. Cell-derived microparticles from platelets (PMP), leukocytes (LMP), endothelium (EMP) were all normal, but RMP were markedly elevated at 4.639/uL, about 3-fold higher than normal controls and more than twice as high as limit for ITP (normal mean=1500/uL; normal ITP mean=2200/uL).

Case study (B). Patient B was found to have ITP in infancy and underwent splenectomy at age 4 months, giving partial remission. Her ITP responded well to glucocorticoids but she tolerated them poorly. Platelets remained usually below 10,000 without treatment. She had heavy menstruation but this did not interfere with her normal activities. During the course of her chronic ITP, now more than 50 years, she carried out normal activities and employment, never experiencing a major bleeding episode nor requiring transfusion. She delivered 2 children without unusual bleeding, and tolerated ankle and knee surgeries. Although she bruised easily on minor trauma and had a few petechiae on careful examination, she never experienced prolonged mucosal bleedings such as nose or gum bleeding, or GI or GU bleedings.

Clinical results: Platelets at 9,000/uL, hemoglobin 13.7, hematocrit 44%, WBC 10,300 with normal differential. Blood chemistries were all within normal limits, as were blood coagulation studies. The patient's antinuclear antibody (ANA) test was negative. Antiphospholipid antibodies and lupus anticoagulant were all negative. Antibodies to platelet glycoproteins IIb/IIIa and Ib/IX were all strongly positive, consistent with ITP. Analysis of her coagulation studies, assays of cell derived microparticles from platelet (PMP), leukocytes (LMP), endothelial cells (EMP) were all within normal limits. Her only abnormality was markedly elevated RMP at 4,438/uL, roughly 2 times higher than usual ITP patients.

The study on these two patients with severe chronic ITP of over 50 years duration revealed that RMP were markedly elevated (unusual compared to other ITP patients) but microparticles derived from other cells such as platelet microparticles (PMP), leukocyte microparticles (LMP) and other laboratory studies were not. These findings support the conclusion that RMP played a key role in protecting them from life-threatening bleeding episodes, since all other laboratory findings were comparable to other ITP patients.

Example 9

In vitro laboratory data supporting that RMP are effective hemostatic agents. We developed several methods to generate RMP in vitro. After generation of RMP, expression of tissue factor (TF) and clotting factor VIII (FVIII) were assayed by immunological methods. In addition, we performed functional tests to determine if RMP can shorten clotting time (50).

Methods

Figure 10:
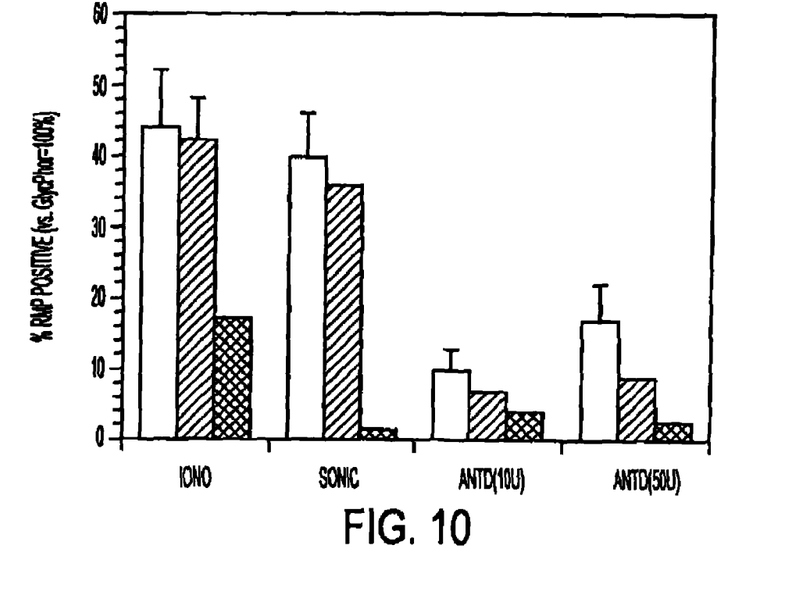
FIG. 10. Expression of TF, FVIII, Annexin V on RMP generated by three methods (ionophore, sonication, and anti-D). The results show positive expression in RMP for TF (shown in empty bars), FVIII (single shaded bars), AnnV (double shaded bars), expressed as a fraction of total RMP; total RMP is defined by number of particles positive for glyocphorin.

We prepared RMP which naturally express TF, FVIII, as described below and shown in FIG. 10. TF-expressing RMP can be used as the basic or universal hemostatic agent in prevention of bleeding in patients with bleeding disorders as well as healthy people at risk of bleeding in situations like surgical or diagnostic procedures. RMP were prepared from freshly drawn normal blood using several methods. Briefly: (a) Ionophore method. Washed RBC were exposed to calcium ionophore in the presence of added calcium. (b) Osmotic shock method. Washed RBC were exposed to hypotonic saline (⅓ of isotonic). (c) Ultrasonic method. Washed RBC were exposed to brief bursts from ultrasound probe (sonication). (d) Anti-D method with/without complement. The starting material was fresh RBC washed 3 times with isotonic saline as usual. Two levels of anti-D (WinRho) were tested, 10 U and 50 U per mL of original blood, added at 50% Ht, then incubated with gentle shaking for 50 min. Then intact RBC were removed by low-speed centrifugation and RMP were pelleted by high-speed centrifugation, as usual, and resuspended for flow cytometry.

Flow cytometry. RMP were identified by fluorescent monoclonal antibody (mAb) against RBC marker glycophorin A. Also measured on RMP by mAb was tissue factor (TF) and clotting factor VIII (FVIII). Fluorescent annexin V (AnV) was employed to measure exposure of procoagulant phosphotidyl serine (PS), and FITC-labeled lectin, *Ulex europaeus* (Ulex) was used to give an estimate of total MP (50).

Flow cytometry revealed that all three methods (a, b, c) yielded abundant RMP. Of special interest is that they express weakly but significantly positive for tissue factor (TF), a potent initiator of coagulation (active at very low levels). FVIII was identified at similar levels. (See FIG. 10).

Representative results of nine experiments by three methods (ionophore, sonication, and anti-D). FIG. 10 shows total RMP as defined by number of particles positive for glyocphorin and that this fraction is positive for TF, FVIII and AnnV. Notice that PS exposure (reflected in AnV positives) is usually low. This suggests a good half-life in circulation because PS is a trigger for phagocytosis.

Procoagulant activity assay of RMP. The RMP from 1.5 mL of RMP prepared in standard way were sedimented by centrifuging 15 min at 8,000×g (Eppendorf microfuge) and the supernatant removed. Then standard (normal) plasma was added, the RMP resuspended. To assess procoagulant activity, RMP is added to the mixture and the recalcification time was measured by adding calcium (2 mM). Clot time was measured manually.

The results (shown in FIG. 11) demonstrate that RMP have significant procoagulant activity, as further detailed below. There are at least two known pathways of blood coagulation. One is an "intrinsic" pathway that is completely inhibited by corn trypsin inhibitor, and a TF mediated "extrinsic" pathway. Without being limited to any particular pathway, the inventors surmise that the because the procoagulant activity of RMP persists in the presence of corn trypsin inhibitor, RMP procoagulant activity is likely due to TF mediation. Not shown are experiments which included corn trypsin inhibitor (which abolishes non-TF mediated procoagulant activity).

Figure 11:
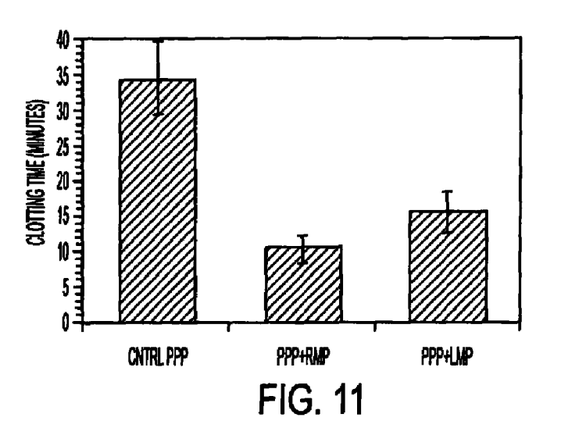

Procoagulant activity of RMP. FIG. 11 shows recalcification clotting time in minutes, mean of replicates +/− standard deviation using the method described above. As can be seen, there is a marked shortening of clotting time in the presence of RMP. Surprisingly, the RMP were more effective in this experiment than a similar quantity of leukocyte-derived MP (LMP) but the difference was not significant. Similar results were confirmed in the presence of corn trypsin inhibitor (50).

Example 10

Figure 12:
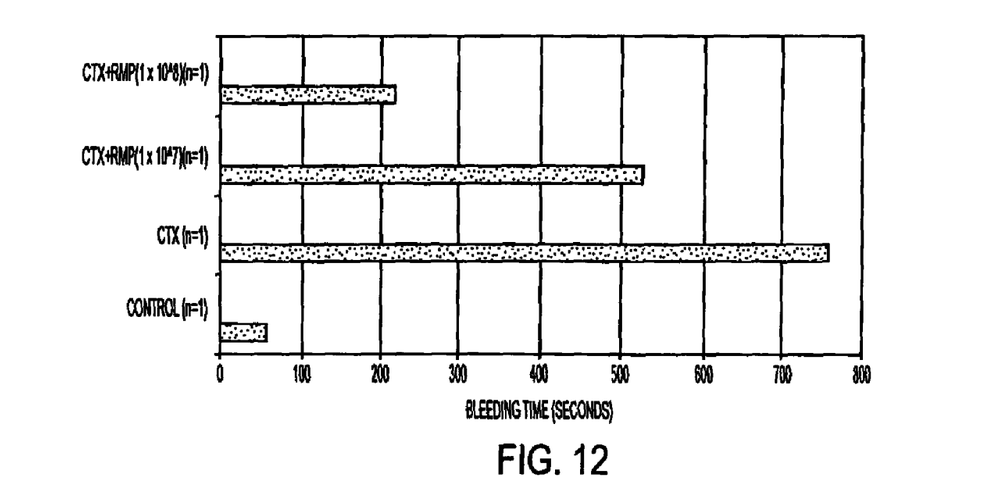

Animal in vivo data demonstrating that RMP are hemostatically active. We studied the efficacy of red blood cell microparticles (RMP) in a dose-dependent manner in adult Fischer rats. The animals were randomized into 4 groups. Group 1 served as normal controls. Groups 2, 3 and 4 were injected i.p. with a single dose of cyclophosphamide (75 mg/kg) to induce thrombocytopenia. At 5 days, when the platelet count was reduced to less than $5 \times 10^5$/microliters in the treated groups, the bleeding time was measured by clipping the tail 2 mm from the tip under anesthesia. Two minutes prior to testing bleeding time, Groups 3 and 4 were injected with $1 \times 10^7$ and $1 \times 10^8$ RMP respectively. RMP were prepared essentially as follows: observing strictly sterile techniques throughout, whole RBC from freshly drawn citrate-treated blood was washed twice with 10 volumes of isotonic saline and then was suspended to 17% hematocrit, then was exposed to ultrasonic burst (Cole-Parmer, Model 4710, Ultrasonic Homogenizer, fitted with small probe) for 1 second. Large debris was removed by low-speed centrifugation (8 min, 200×g in Beckman clinical centrifuge, then the supernatent was centrifuged for 15 min at 8,000×g in Eppendorf microfuge (in 1.5 mL polypropylene tubes) and the burgundy-colored supernatant was removed. The small pellet of RMP was suspended in a small volume, counted by FITC-labeled *Ulex europaeus*, and then diluted to the concentration indicated prior to injection in the experimental animal The results are shown in FIG. 12. In normal controls, bleeding time was less than one minute. Group 2, after thrombocytopenia induction and which received cyclophosphamide only, had a bleeding time of over 700 seconds. Group 3, which received $1 \times 10^7$ RMP after thrombocytopenia induction, had a greatly reduced bleeding time compared to group 2. A dose-dependent effect was observed of RMP administration, with a still greater decrease in bleeding time observed in animals treated with $1 \times 10^8$ RMP.

Example 11

Conjugation of clotting factors or adhesions to RMP. RMP can be biochemically modified to augment their hemostatic activity for some applications. For example, RMP may be modified by ultrasonic incorporation of polyethylene glycol (PEG) since it has been shown that PEGylated liposomes then avidly but non-covalently adsorb both FVIII and vWf (55). In another approach, RMP may be modified by the covalent addition of RGD peptide [53,62]. Methods for conjugation of specific proteins or peptides to phospholipids (PL) vesicles are well-known in the art, see in particular the comprehensive text by Greg T. Hermanson, *Bioconjugate Techniques* (54). Since cell derived microparticles are essentially PL vesicles, it is reasonably expected that the same methods are applicable.

It is envisioned that the agent to be conjugated to RMP (e.g. RGD peptide) can be pre-activated intermediates and stored in sterile lyophilized form (for example, see (54), (page 236). When needed, it may be added to the patient RMP, resulting in protein-RMP conjugates after one hour incubation, then requiring only that the conjugated RMP be washed free of excess of reagents.

References Cited Herein are Hereby Incorporated by Reference and are Listed Below for Convenience 1. Horstman L L, Ahn Y S. Platelet microparticles: A wide-angle perspective (Review). Crit. Rev Oncol/Hematol 1999; 30: 111-142.
2. Horstman L L, Jy W, Jimenez J J, Ahn Y S. Endothelial microparticles as markers of endothelial dysfunction (Review). Frontiers in Bioscience 2004; 9: 1118-1135.
3. Ahn Y S. Cell-derived microparticles: Miniature envoys with many faces. J Thromb and Hemostasis. 3:884-887, May, 2005.
4. Dachary-Prigent J D, Freyssinet J-M, Pasquet J-M, Carron J-C, Nurden A T. Annexin V as a probe of aminophospholipid exposure and platelet membrane vesiculation: A flow cytometric study showing a role for free sulfhydryl groups. Blood 1993; 81: 2554-2565.
5. Mallat Z, Hugel B, Ohan J, Leseche G, Freyssinet J N, Tedgui A. Shed membrane microparticles with procoagulant potential in human atherosclerotic plaques: A role for apoptosis in plaque thrombogenicity. Circulation 1999; 99:348-353.
6. Zwaal R F A, Schroit A J. Pathophysiologic implications of membrane phospholipid asymmetry in blood cells. Blood 1997; 89: 1121-1132.
7. Sims P J, Wiedmer T. Unraveling the mysteries of phospholipid scrambling. Thromb Haemost 2001; 86: 266-275.
8. Jy W, Horstman L L, Wang F, Duncan R, Ahn Y S. Platelet factor 3 in plasma fractions: Its relation to microparticle size and thromboses. Thromb Res 1995; 80: 471-482.
9. Satta N, Toti F, Feugeas O et al. Monocyte vesiculation as a possible mechanism of dissemination of membrane-associated procoagulant activities and adhesion molecules after stimulation by lipopolysaccharide. J Immunol 1994; 153:3245-3255.
10. Biro E, Sturk-Maquelin K N, Vogel G M Human cell-derived microparticles promote thrombus formation in vivo in a tissue factor-dependent manner. J Thromb Haemost. 2003; 1:2561-8.
11. Shet A S, Aras O, Gupta K et al. Sickle blood contains tissue factor-positive microparticles derived from endothelial cells and monocytes. Blood. 2003; 102:2678-83.
12. Combes V, Simon A C, Grau G E et al. In vitro generation of endothelial microparticles and possible prothrombotic activity in patients with lupus anticoagulant. J Clin Invest 1999; 104: 93-102.
13. Abid Hussein M N, Meesters E W, Osmanovic N, Romijn F P, Nieuwland R, Sturk A. Antigenic characterization of endothelial cell-derived microparticles and their detection ex vivo. J Thromb Haemost. 2003; 1:2434-43.
14. Jimenez J, Jy W, Mauro L, Horstman L, Ahn Y. Elevated endothelial microparticles in thrombotic thrombocytopenic purpura (TTP): Findings from brain and renal microvascular cell culture and patients with active disease. Br J Haematol 2001; 112: 81-90.
15. Siddiqui F A, Desai H, Amirkhosravi A, Amaya M, Francis J L. The presence and release of tissue factor from human platelets. Platelets. 2002; 13:247-53.
16. Jy W, Mao W W, Horstman L L, Tao J, Ahn Y S. Platelet microparticles bind, activate and aggregate neutrophils in vitro. BCMD (Blood Cells, Molecules and Diseases) 1995; 21: 217-231.
17. Barry O P, Pratico D, FitzGerald G. Platelet microparticles enhance adhesive interactions between monocytes and endothelial cells. J Clin Invest 1997; 45: 271A
18. Barry O P, Pratico D, Savani R C, FitzGerald G A. Modulation of monocyte-endothelial cell interactions by platelet microparticles. J Clin Invest 1998; 102: 136-144.

19. Mesri M, Altieri D C. Leukocyte microparticles stimulate endothelial cell cytokine release and tissue factor production in a JNK1 signalling pathway. J Biol Chem 1999; 274: 23111-23118.
20. Freyssinet J M. Cellular microparticles: what are they bad or good for? J Thromb Haemost 2003; 1: 1655-1662.
21. Ware J A, Heistad D D. Platelet-endothelium interactions. N Engl J Med 1993; 328(9): 628-635.
22. Marcus A J, Broekman M J, Drosopoulos J H F et al. The endothelial cell ecto ADPase responsible for inhibition of platelet function is CD39. J Clin Invest 1997; 99: 1351-1360.
23. Moncada S, Vane J R. Prostacyclin and its clinical applications. Ann Clin Res 1984; 16(5-6): 241-252.
24. Alonso D, Radomski M W. Nitric oxide, platelet function, myocardial infarction and reperfusion therapies. Heart Fail Rev 2003; 8: 47-54.
25. Bombeli T, Schwartz B R, Harlan J M. Endothelial cells undergoing apoptosis become proadhesive for nonactivated platelets. Blood 1999; 93: 3831-3838.
26. Ruggeri Z M. Von Willebrand factor, platelets and endothelial cell interactions. J Thromb Haemost 2003; 1: 1335-1342.
27. Wilson J M, Ferguson J J. Platelet-endothelial interactions in atherothrombotic disease: therapeutic implications (Review). Clin Cardiol 1999; 22: 687-698.
28. Fisher A B, Chien S, Barakat A I, Nerem R M. Endothelial cellular response to altered shear stress. Am J Physiol Lung Cell Mol Physiol 2001; 281: L529-533.
29. Miyazaki Y, Nomura S, Miyake T et al. High shear stress can initiate both platelet aggregation and shedding of procoagulant containing microparticles. Blood 1996; 88: 3456-3464.
30. Cheresh D A, Berliner S A, Vicente V, Ruggeri Z M. Recognition of distinct adhesive sites on fibrinogen by related integrins on platelets and endothelial cells. Cell 1989; 58: 945-953.
31. Frenette P S, Johnson R C, Hynes R O, Wagner D D. Platelets roll on stimulated endothelium in vivo: an interaction mediated by endothelial P-selectin. Proc Natl Acad Sci USA 1995; 92: 7450-7455.
32. Andre P, Denis C V, Ware J et al. Platelets adhere to and translocate on von Willebrand factor presented by endothelium in stimulated veins. Blood 2000; 96: 3322-3328.
33. Jimenez J J, Jy W, Mauro L M, Horstman L L, Soderland C, Ahn Y S. Endothelial microparticles released in thrombotic thrombocytopenic purpura express von Willebrand factor and markers of endothelial activation. Br J Haematol 2003; 123: 896-902.
34. Jimenez J J, Jy W, Mauro L, Soderland C, Horstman L L, Ahn Y S. Endothelial cells release phenotypically and quantitatively distinct microparticles in activation and apoptosis. Thromb Res 2003; 109: 175-180.
35. Jy W, Horstman L L, Park H, Mao W W, Valant P, Ahn Y S. Platelet aggregates as markers of platelet activation: Characterization of flow cytometric method suitable for clinical applications. Am J Hematol 1998; 57: 33-42.
36. Raines G, Aumann H, Sykes S, Stree A. Multimeric analysis of von Willebrand factor by molecular sieving electrophoresis in sodium dodecyl sulfate agarose gel. Thromb Res 1990; 60: 201-212.
37. Nakane P K. Simultaneous localization of multiple tissue antigens using the peroxidase-labeled antibody method: a study on pituitary glands of the rat. J Histochem Cytochem 1968; 16(9): 557-560.
38. Levy G G, Nichols W C, Lian E C, et al. Mutations in a member of the ADAMTS gene family cause thrombotic thrombocytopenic purpura. Nature 2001; 413: 488-494.
39. Moake J L. Thrombotic microangiopathies. N Engl J Med 2002; 347: 589-600.
40. Sabatier F, Roux V, Anfosso F, Camoin L, Sampol J, Dignat-George F. Interaction of endothelial microparticles with monocytic cells in vitro induces tissue factor-dependent procoagulant activity. Blood 2002; 99: 3962-3970.
41. Jy W, Minagar A, Jimenez J J, et al. Endothelial microparticles (EMP) bind to monocytes to activate and enhance transmigration: Elevated circulating EMP-monocyte conjugates in multiple sclerosis. Frontiers Biosci 2004; 9:3137-44.
42. Gawaz M, Neumann F J, Dickfeld T et al. Vitronectin receptor (alpha-V-beta-3) mediates platelet adhesion to the luminal aspect of endothelial cells. Circulation 1997; 96: 1809-1818.
43. J. Arnout, E. Huybrechts, M. Vanrusselt, J. Vermylen: A new lupus anticoagulant test based on platelet-derived vesicles. *Brit J Haemat* 1992; 80: 341-346.
44. Fiebig E W, Busch M P, Menitove J E: Transfusion transmitted diseases 2527-40. In Hematology, 4th edition, 2005. Elesvier Inc. (Edit) Hoffman R
45. Wu Y Y, Snyder E L: Transfusion Reactions 2515-26. In Hematology, 4th edition, 2005. Elesvier Inc. (Edit) Hoffman R et al.
46. Meier L G, Barthel H R, Seidl C: Development of polyarthritis after insertion of silicone breast implants followed by remission after implant removal in 2 HLA-identical sisters bearing rheumatoid arthritis susceptibility genes. J. Rheumatology. 1997 24 (9): 1838-41.
47. Tenenbaum S A, Rice J C, Espinoza L R et al: Use of antipolymer antibody assay in recipients of silicone breast implants. Lancet 1997 349 (9050): 449-54, 1997.
48. Zandaman-Goddard G, Blank M, Ehrenfield M et al: A comparison of autoantibody production in asymptomatic and symptomatic women with silicone breast implants. J Rhematology. 26 (1): 73-7.
49. Janowsky E C, Kupper L L, Hulka B S: Meta-analysis of the relation between silicone breast implants and the risk of connective-tissue diseases. NEJM 342(11):781-90, 2000.
50. Ahn Y S et al: Extremely high RMP levels among patients with severe ITP who manifest little sign of bleeding. (manuscript in preparation).
51. Jy W, Horstman L, Ahn Y S et al: Hemostatic property of RMP measured in vitro. (manuscript in preparation).
52. Macchi L et al: PAICA: a Method for characterizing platelet-associated antibodies. Thrombosis and Haemostasis 76:1020-9, 1996.
53. BS Coller, et al: Thromboerythrocytes: In vitro studies of a potential autologous, semi-artificial alternative to platelet transfusions. *J Clin Invest* 1992; 89(February): 546-55.
54. G T Hermanson: *Bioconjugate Techniques.* New York: Academic Press, 1996.
55. M Baru, EtAl: Factor VIII efficient and specific non-covalent binding to PEGylated liposomes enables prolongation of its circulation time and hemostatic efficiency. *Thromb Haemost* 2005; 93(1061-1068).
56. G Agam, A A Livne: Erythrocytes with covalently bound fibrinogen as a cellular replacement for the treatment of thrombocytopenia. *Eur J Clin Invest* 1992; 22(2): 105-12.
57. M Levy, et al: Fibrinogen-coated albumin microcapsules reduce bleeding in severely thrombocytopenic rabbits. *Nat Med* 1999; 5(1): 107-11.

58. Y Teramura, et al: Hemostatic effects of polymerized albumin particles bearing rGP Ia/IIa in thrombocytopenic mice. *Biochem Biophys Res Com* 2003; 306: 256-60.
59. T Nishaya, et al: Targeting of liposome carrying recombinant fragments of platelet membrane glycoprotein 1b-alpha to immobilized von Willebrand factor underflow conditions. *Biochem Biophys Res Com* 2000; 270(755-760).
60. T Nishaya, et al: Reconstitution of adhesive properties of human platelets in liposomes carrying both recombinant glycoproteins Ia/IIa and Ib-alpha under flow conditions: specific synergy of receptor-ligand interactions. *Blood* 2002; 100(1): 136-42.
61. T Kamata, et al: Membrane-proximal alpha/beta stalk interactions differentially regulate integrin activation. *J Biol Chem* 2005; 280(26): 24775-83.
62. A S Gupta, et al: RGD-modified liposomes targeted to activated platelets as a potential vascular drug delivery system. *Thromb Haemost* 2005; 93(1): 106-14.
63. W Jy, J J Jimenez, L L Horstman, L Mauro, C Bidot Jr, M Yaniz, M Gonzalez, E R Ahn, C J Bidot and Y S Ahn. Microparticles Derived from Platelets (PMP), Endothelia (EMP), and Leukocytes (LMP) Exhibit Distinctive Hemostatic and Inflammatory Activities. Blood 2005; 106(11): 1029a. [To be presented at the meeting of American Society of Hematology in Dec. 12, 2005 at Atlanta, Ga.]
64. A Gennaro, ed. *Remington's Pharmaceutical Sciences,* 1990; Mack Pub.

We claim:

1. A method of increasing hemostasis comprising administering a composition comprising cell-derived microparticles that are effective to treat an excessive bleeding condition in a mammal in need thereof, wherein said microparticles are red cell derived microparticles (RMP).

2. The method of claim 1 wherein the mammal is a human.

3. The method of claim 1 wherein the excessive bleeding condition is caused by a clinical disorder.

4. The method of claim 2 wherein the human suffers from a blood clotting disorder.

5. The method of claim 2 wherein the human suffers from a disease or disorder selected from the group consisting of immune or idiopathic thrombocytopenic purpura, drug- and chemotherapy-induced thrombocytopenia, thrombocytopenias of different causes both congenital and acquired, and impaired platelet function, both congenital and acquired.

6. The method of claim 3 wherein the thrombocytopenia is induced by a chemotoxic agent.

7. The method of claim 6 wherein the chemotoxic agent is administered during chemotherapy.

8. The method of claim 1 wherein excessive bleeding condition is caused by a traumatic injury or is undergoing surgical procedures or invasive diagnostic or therapeutic procedures where bleeding and blood loss can be substantial.

9. The method of claim 1 wherein the RMP have been derived from the red blood cells of the individual to whom they are being administered.

10. A method of treating an excessive bleeding condition comprising administering a composition comprising red cell-derived microparticles that promote formation of blood clots and stimulate platelet adhesion and aggregation to a patient in need thereof.

11. The method of claim 1 wherein the dosage of microparticles is between $10^6$ and $10^{12}$/kg.

12. The method of claim 11 wherein the dosage is between $10^8$ and $10^{10}$/kg.

13. The method of claim 1 wherein the composition is administered intravenously.

\* \* \* \* \*